(12) United States Patent
Huguenin et al.

(10) Patent No.: US 7,172,420 B2
(45) Date of Patent: Feb. 6, 2007

(54) ULTRASONIC SHAPING INSTRUMENT

(75) Inventors: Gérard Huguenin, Villeret (CH); Pierre Pasche, St-Imier (CH)

(73) Assignee: Ecole D'Ingenieurs, St. Imier (CH)

( * ) Notice: Subject to any disclaimer, the term of this patent is extended or adjusted under 35 U.S.C. 154(b) by 462 days.

(21) Appl. No.: 10/479,165

(22) PCT Filed: May 15, 2002

(86) PCT No.: PCT/CH02/00266

§ 371 (c)(1),
(2), (4) Date: Apr. 30, 2004

(87) PCT Pub. No.: WO02/094120

PCT Pub. Date: Nov. 28, 2002

(65) Prior Publication Data

US 2004/0170944 A1 Sep. 2, 2004

(30) Foreign Application Priority Data

May 25, 2001 (EP) .................................. 01810514

(51) Int. Cl.
*A61C 1/07* (2006.01)
*A61C 3/08* (2006.01)

(52) U.S. Cl. ........................................ 433/119; 433/86

(58) Field of Classification Search ................ 433/119, 433/86, 88
See application file for complete search history.

(56) References Cited

U.S. PATENT DOCUMENTS

| 4,371,816 A | 2/1983 | Wieser ........................ 318/116 |
| 5,059,122 A | 10/1991 | Hetzel ......................... 433/118 |
| 5,294,896 A | 3/1994 | Kjellander .................. 331/158 |
| 6,190,167 B1 | 2/2001 | Sharp ......................... 433/119 |

FOREIGN PATENT DOCUMENTS

WO  WO 89/01763  3/1989

*Primary Examiner*—Cris L. Rodriguez
*Assistant Examiner*—Candice C. Stokes
(74) *Attorney, Agent, or Firm*—Hugh R. Kress; Browning Bushman P.C.

(57) ABSTRACT

The invention concerns an ultrasonic shaping instrument comprising: a mount structure (10), a sonotrode (14) elastically mounted on the mount structure (10), a tool (16) fixed to the sonotrode (14) for carrying out shaping operations, and a control member (12) for controlling and powering the sonotrode (14). The instrument is dimensioned so that the assembly consisting of the sonotrode (14) and the tool (16) has a resonance ultrasonic frequency fo, in a mode selected among traction-compression and torsion, variable between a lower limit fomin and an upper limit fomax, and it does not have itself any other resonance frequency in a range between a frequency fpmin<fomin and a frequency fpmax>fomax.

20 Claims, 2 Drawing Sheets

ULTRASONIC SHAPING INSTRUMENT

The present invention relates to ultrasonic shaping instruments, of the type including:
- a mount structure
- a sonotrode elastically mounted on the mount structure,
- a tool fixed to the sonotrode for carrying out shaping operations, and
- a control unit for controlling and powering the sonotrode.

"Shaping" means any mechanical operation tending to modify the structure of an object by the mechanical removal of matter or by fusion.

An instrument of this type is, for example, disclosed in WO Patent No. 89/01763. This instrument is for removing tartar from teeth, by means of a scraper actuated by a low amplitude movement at an ultrasonic frequency, breaking the tartar and thus removing it from the tooth. The control unit is an amplifier type circuit which, coupled to the sonotrode, forms an oscillator whose frequency is given by the features of the instrument. This frequency varies, in particular, with temperature, which can increase, via Joule effect, when the instrument is operating.

The use of an amplifier type circuit allows satisfactory working conditions. It is however relatively expensive, becoming more so the larger the power in play, taking account of the available volume.

It is an object of the present invention to allow a simplified control unit to be used, arranged to apply a signal across the transducer terminals that does not vary as a function of the features of the instrument. It is, consequently, no longer necessary to have a servo-system, which leads to simplification and reduced volume.

This object is achieved due to the fact that the instrument is dimensioned such that:
- the assembly formed by the sonotrode and the tool has an ultrasonic resonant frequency fo, in a mode selected from among traction-compression and torsion, capable of varying between a lower limit fomin and an upper limit fomax, and
- it does not itself have any other resonant frequency within a range comprised between a frequency fpmin<fomin and a frequency fpmax>fomax, the control unit being of the type generating a sinusoidal signal frequency modulated by a quasi-random signal, so as to apply an electric pass band signal comprised between a minimum frequency femin and a maximum frequency femax, femin being comprised within the interval fpmin–fomin and femax in the interval fomax–fpmax.

A "quasi-random signal" means a random or pseudo random signal, such as those capable of being generated by computer programs by means of a shift register, for example. The natural frequency fo should be considered as a spectrum of frequencies, the maximum of which is at value fo. The width of the spectrum is essentially a function of the structure of the sonotrode and working conditions. The absence of any resonant frequency other than fo in the range being considered is to be taken in the relative sense. In practice, a ratio of four to one between the level of energy at the frequency fo being considered and that within the remainder of the range fpmin–fpmax is already sufficient to obtain acceptable working conditions.

With an instrument like that described above, the sonotrode is powered by the signal component corresponding to its instantaneous natural frequency. Indeed, since the interval fomin–fomax is comprised within the interval femin–femax, maintenance can be carried out in the whole of the instrument's operating range. Moreover, as there is no other resonant frequency in the interval fpmin–fpmax, which contains the interval femin–femax, there is no risk of the instrument beginning to oscillate at a stray frequency, which would have the effect of reducing efficiency and causing heating that could go as far as to prevent continuous working.

In this instrument, the control unit can include a power circuit and a control circuit driving the power circuit, the latter being formed of an E type amplifier, whereas the sonotrode includes a piezoelectric transducer. More precisely, the power circuit includes a power transistor and a transformer, the transformer primary winding being connected to the transistor and the secondary winding to the piezoelectric transducer.

Depending upon the application, it is useful to vary the power available on the tool. This can easily be achieved by having a control unit allowing the values of femin and/or femax to be varied. It appears that the more the femin–femax interval increases, the more the power available for the frequency fo being considered decreases. More precisely, the available power is inversely proportional to the variation in bandwidth.

Advantageously, the sonotrode works in a traction-compression mode, its frequency being higher than 20 kHz.

In order to allow the instrument to be handled, its mount structure is formed of a sleeve inside which the sonotrode is mounted.

In order to ensure optimum working conditions for the sonotrode, it includes an inertia mass and a head. It is mounted on the sleeve by two elastic members one cooperating with the mass, the other with the head, whereas the tool is rigidly mounted on the head. The piezoelectric transducer is interposed between the head and the mass.

These instruments allow, in particular, shaping by scraping, which is possible when the tool has a scraper shape, particularly arranged for removing tartar from teeth.

Other features and advantages of the invention will appear from the following description, made with reference to the annexed drawing, in which.

Figure 1:
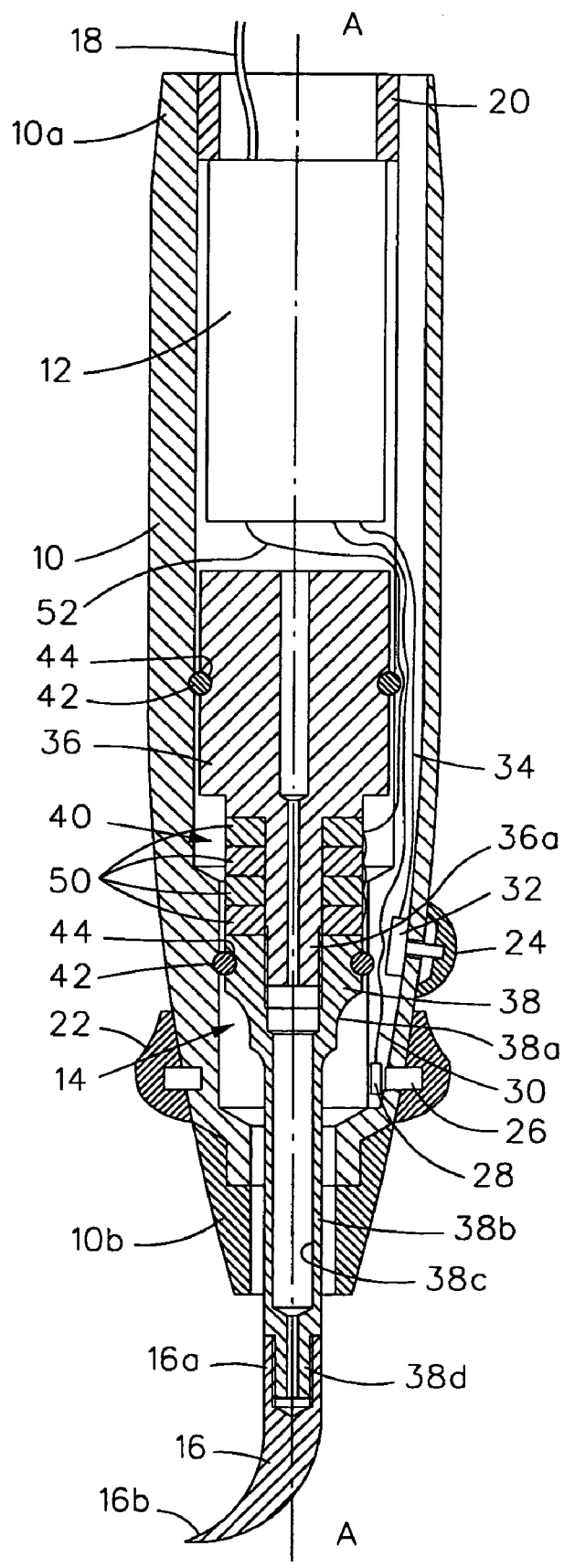
FIG. 1 shows the components of an instrument according to the invention.

The instrument shown in FIG. 1 is for removing tartar from teeth. It essentially includes a mount structure formed of a sleeve 10 and, housed inside the latter, a control unit 12 which will be described in detail with reference to FIG. 2 and a sonotrode 14, as well as a tool formed of a scraper 16, rigidly fixed to the sonotrode 14, by screwing, and arranged outside sleeve 10. Control unit 12 is powered by an electric energy source that is not shown, by means of a cable 18 exiting one of the ends of sleeve 10.

Sleeve 10 is formed of a substantially cylindrical tube, of axis A—A, made of stainless steel or synthetic material. One of its ends 10a is partially closed by an annular cap 20 holding unit 12 inside sleeve 10 and through which cable 18 passes. The other end 10b includes an aperture in which the end of sonotrode 14 carrying scraper 16 is engaged. Sleeve 10 can be made in one piece or made of rings cooperating with each other and fixed to each other by screwing or welding. The use of rings facilitates the positioning of control unit 12 and sonotrode 14.

Sleeve 10 carries, in its portion next to its end 10b, a control ring 22 for adjusting the power available on scraper 16 and a button 24 able to move longitudinally and controlling the switching on and off of the instrument.

Control ring 22 is provided with an annular multipolar magnet 26, which controls a magneto-sensitive contactor 28 fixed inside sleeve 10 and electrically connected to control unit 12 by a conductor 30, ring 22 and contactor 28 being arranged such that the rotational direction of ring 22 can be identified by unit 12.

Button 24 controls a switch 32 that is also mounted on sleeve 10 and connected to unit 12 by a conductor 34 to control the switching on and off of power to sonotrode 14 which starts scraper 16 moving.

Sonotrode 14 includes an inertia mass 36, a head 38 and a piezoelectric transducer 40 inserted between head 38 and mass 36. It is elastically mounted inside sleeve 10 by means of two O-rings 42, made of elastic material, engaged in grooves 44 one of which is made in head 38, the other in mass 36, and abutting against sleeve 10.

Inertia mass 36 is chosen to be as heavy as possible, within acceptable limits to allow it to be hand held properly, such that the movement generated by the piezoelectric transducer is essentially imparted to scraper 16, the rest of the instrument remaining substantially still. It is extended in the direction of head 38 by a rod 36a on which transducer 40 is engaged, and whose end is provided with an internal screw thread 36b.

Head 38 has a general cannula shape, including a ring 38a screwed onto rod 36a and abutting against transducer 40, in which groove 44 is made. Ring 38a is extended by a tube 38b, pierced right through with a channel 38c, of which the end opposite the ring is provided with a thread 38d onto which scraper 16 is fixed.

Hole 38c has the function of adjusting the resonant frequencies of the head. The diameter of hole 38c and the thickness of the walls of tube 38b are selected empirically, as a function of the general shape of the various active parts of the instrument. Indeed, a modification in the diameter of the hole changes the resonant frequencies of the traction compression, torsion or bending modes in a different way. It is thus possible to offset these resonant frequencies, by acting on the diameter of hole 38c and on the thickness of tube 38b.

Head 38 is advantageously made of a light metal, for example titanium, such that its inertia is as low as possible, while having minimum internal friction.

The shape of head 38 is selected such that the motion of scraper 16 is as broad as possible. Considerations in this regard are set out in WO Patent No. 89/01763 cited hereinbefore. They will not, therefore, be explained in more detail here.

Transducer 40 is formed of four discs 50 made of piezoelectric material such as those sold, for example, by Philips (Eindhoven NL) under the reference 4322 020 0659. These discs 50 have an external diameter of 10 mm, a central aperture with a diameter equal to 5 mm and a thickness of 2 mm. They are coated, on their two flat faces, with a layer of conductive material, having the function of an electrode. Discs 50 are connected in parallel and connected to unit 12 on the one hand by the electrical earth, and on the other hand by a conductor 52, as described for example in WO Patent No. 89/01763. Usually, the piezoelectric transducer works in a traction-compression mode. It is, however, also possible to envisage a torsion mode. A shearing mode does not seem to have any particular application.

Head 38 is screwed onto mass 36 so as to pre-stress piezoelectric discs 50 in order that, even when they are compressed via the piezoelectric effect, there is no play between them and with mass 36 and head 38.

Scraper 16 includes a portion 16a, securing it onto end 38d of head 38 which is provided, for this purpose, with a threaded hole, and an active part 16b ensuring the shaping function. The material of which it is formed is chosen to be sufficiently hard to attack the tartar deposited on the tooth to be treated, but not too much, so as to avoid damaging the enamel.

The features of all of the sonotrode components and scraper 16 that it carries, define its natural frequency fo. This frequency is generally higher than 20 kHz, typically 25 kHz. It can vary between a value fomin and fomax, particularly as a function of the working temperature and charge applied to the scraper. This variation is of the order of ±1%.

Tests have been carried out with a sonotrode having the following features. The titanium inertia mass 36 has a total length equal to 30 mm, rod 36a having a length of 12.5 mm and a diameter of 4.2 mm. It is pierced axially over a length of 16 mm with a diameter of 2 mm in its portion having the largest diameter, whereas in part 36a, the diameter is 1 mm. Head 38 is also made of titanium. Ring 38a includes a cylindrical portion with a diameter equal to 10 mm and a length substantially equal to 3 mm. Tube 38b has a diameter of 4 mm, a length substantially equal to 20 mm and a wall thickness equal to 0.4 mm. End 38d has a length of 6 mm, of which 4.5 mm are threaded. It is pierced with a hole 1 mm in diameter. The device obtained demonstrated a traction-compression resonant frequency at 24.3 kHz, and stray bending frequencies at 21.2 and 35.2 kHz, the amplitudes being respectively ⅓ and ⅑ of the amplitude at frequency fo.

The frequencies obtained with the example described are specified in the table below:

| Parameter | fo | fomin | fomax | femin | femax | fpmin | fpmax |
| --- | --- | --- | --- | --- | --- | --- | --- |
| Frequency [kHz] | 24.3 | 24.05 | 24.55 | 21.2–24.05 | 24.55–35.2 | 21.2 | 35.2 |

It thus clearly appears that the ranges within which femin and femax can vary are broad, which allows a large range for adjusting the power provided to scraper 16.

Figure 2:
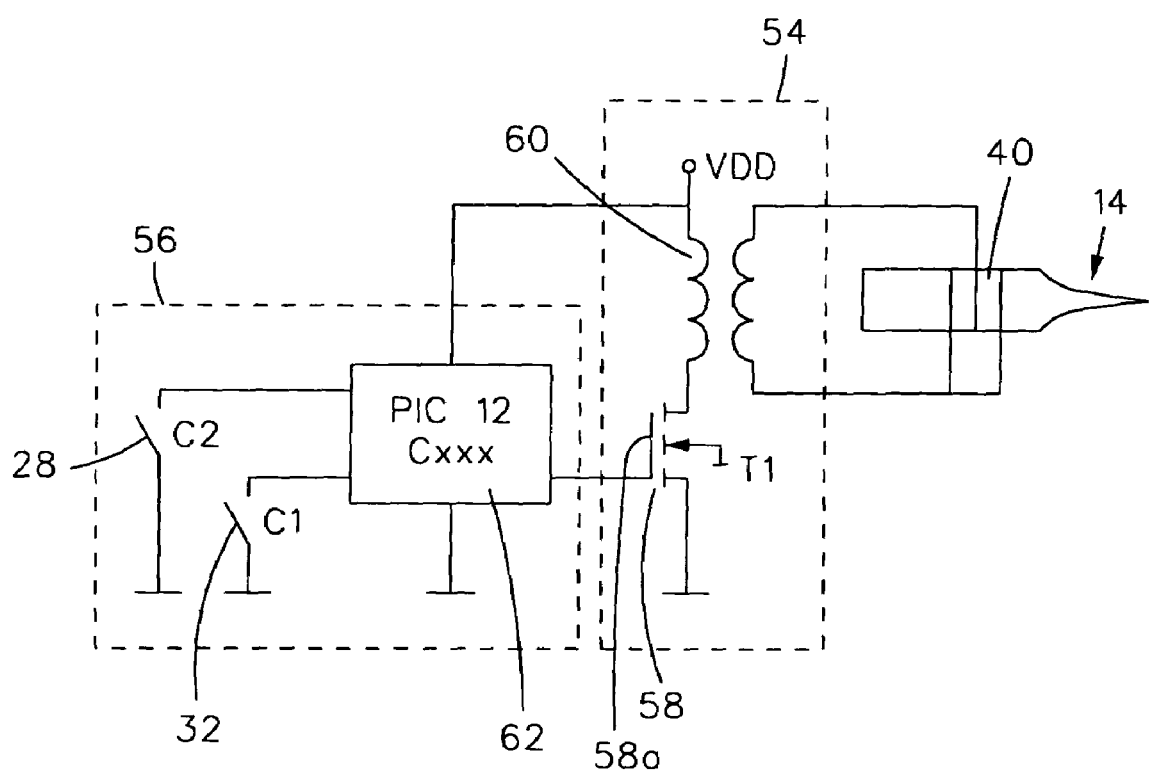
FIG. 2 is a diagram of the control unit of the instrument.

Control unit 12 is shown in FIG. 2. It includes a power circuit 54, powering sonotrode 14, and a control circuit 56 driving power circuit 54.

Power circuit 54 is an E class amplifier. It includes a BUZ 11 type power transistor 58 like that marketed by Infineon Technologies (Munich, Germany), and a transformer 60 whose primary winding is connected to power source VDD and to transistor 58, whereas the secondary winding is connected to the terminals of transducer 40. Transformer 60 is dimensioned such that the voltage across the terminals of transducer 40 is sufficient to dispense the power required for the tartar removing operations. Practice has shown that an efficient voltage of the order of 400V is sufficient.

Control circuit 56 includes contactor 28 and switch 32, as well as a microprocessor 62, for example of the PIC 12 Cxxx type, as sold by Microchip Chandler, Ariz. (USA).

Microprocessor 62 is provided with a memory containing data relating to the state of contactor 28 and switch 32, and its operating program.

The mission of microprocessor 62 is to check the state of switch 32. While the latter is open, the other programs are on standby.

When switch 32 is closed, microprocessor 62 will search the memory for data from contactor 28, such data can be modified by rotating ring 22 in one direction or the other, which increments or decrements the content of the memory. From this data, microprocessor 62 generates a carrier signal whose frequency femoy is close to the resonant frequency fo of sonotrode 14 and a pseudo-noise generated by the use of a shift register, as explained in the McMOS Handbook, section E, MOTOROLA 1974. The bandwidth of the pseudo-noise, defined by a minimum frequency femin and a maximum frequency femax, is greater the higher the memory content.

The signal, modulated by the pseudo-noise is applied to grid 58*a* of transistor 58, in the form of pulses, current amplified by transistor 58 and voltage amplified by transformer 60. Sonotrode 14 is powered by the portion of the signal coinciding with its resonance spectrum. Consequently, the energy provided is greater the narrower the band defined by femin and femax. By varying femin and/or femax, it is thus possible to adjust the power provided to scraper 16 by sonotrode 14.

With this control, the signal derived from the microprocessor can remain the same, despite changes in the natural frequency fo of the sonotrode, provided fomin and femax remain within the femin–femax interval.

It is, consequently, possible to carry out maintenance of an instrument like that described with a control unit of great simplicity. It is however necessary to take a particular precaution. Indeed, if the instrument had one or more natural frequencies in the femin–femax interval, it would also be vibrating, the energy then being dissipated in pure waste, causing, moreover, the instrument to heat up. This problem can be avoided by adjusting the components of the instrument such that it does not have any other resonant frequency in a range comprised between fpmin<femin and fpmax>femax.

In order to satisfy this requirement, it is desirable for the instrument to be as rigid as possible in its structure and to adjust the dimensions of its various components so as to achieve this object.

In practice, the various components are dimensioned such that this rigidity is obtained, then the sonotrode is powered by means of a variable frequency signal, so as to show the resonant frequencies. Its dimensions are adjusted to obtain a frequency suited to the features of the instrument, while eliminating the stray frequencies. This dimensioning is carried out by trial and error, by modifying the inertia of the sonotrode, essentially at mass 36 and head 38, or its elastic structure, essentially formed by rod 48.

Practice shows that the constituent parts of the instrument are sufficiently precise for its natural frequencies not to change substantially from one of these instruments to another. An end of manufacturing check is however desirable, especially when a stray resonant frequency is close to one or other of frequencies fpmin and fpmax.

It is clear that the instrument as described can be subject to numerous variants, without however departing from the scope of the invention. It is thus possible to use such an instrument for deburring, cutting or etching work, or even for carrying out ultrasonic micro-welds. In each of these applications, the tool is adapted to the shaping operation to be carried out, while taking account of the influence that it has on any stray frequencies of the instrument.

The invention claimed is:

1. Ultrasonic shaping instrument including:
   a mount structure (10),
   a sonotrode (14) elastically mounted on the mount structure (10),
   a tool (16) fixed to the sonotrode (14) for carrying out shaping operations, and
   a control unit (12) for controlling and powering the sonotrode (14), characterized in that it is dimensioned such that:
   the assembly formed by the sonotrode (14) and the tool (16) has an ultrasonic resonant frequency fo, in a mode selected from among traction-compression and torsion, capable of varying between a lower limit fomin and an upper limit fomax, and
   it does not itself have any other resonant frequency within a range comprised between a frequency fpmin <fomin and a frequency fpmax> fomax,
   and in that the control unit (12) is of the type generating a sinusoidal signal frequency modulated by a quasi-random signal, so as to apply a passband electric signal comprised between a minimum frequency femin and a maximum frequency femax, femin being comprised in the interval fpmin–fomin and femax in the interval fomax–fpmax.

2. Instrument according to claim 1, characterized in that said tool has the shape of scraper (16).

3. Instrument according to claim 2, characterized in that said scraper (16) is arranged for removing tartar from teeth.

4. Instrument according to claim 1, characterized in that said control unit (12) includes a power circuit (54) and a control circuit (56) driving the power circuit (54), which is formed of an E type amplifier, and in that said sonotrode (14) includes a piezoelectric transducer (40).

5. Instrument according to claim 4, characterized in that said tool has the shape of scraper (16).

6. Instrument according to claim 4, characterized in that said mode is a traction-compression mode and its frequency fo is higher than 20 kHz.

7. Instrument according to claim 6, characterized in that said mount structure is formed of a sleeve (10), inside which said sonotrode (14) is mounted.

8. Instrument according to claim 4, characterized in that said mount structure is formed of a sleeve (10), inside which said sonotrode (14) is mounted.

9. Instrument according to claim 8, characterized in that said sonotrode (14) includes an inertia mass (36) and a head (38), in that it is mounted on said sleeve (10) by two elastic members (42), one cooperating with the mass (36), the other with the head (38), and in that said tool (16) is rigidly mounted on said head (38).

10. Instrument according to claim 9, characterized in that said transducer (14) is interposed between said mass (36) and said head (38).

11. Instrument according to claim 4, characterized in that said control circuit (12) includes means (22) for varying the passband femin–femax, and thus modifying the energy provided to the tool (16).

12. Instrument according to claim 11, characterized in that said mode is a traction-compression mode and its frequency fo is higher than 20 kHz.

13. Instrument according to claim 11, characterized in that said mount structure is formed of a sleeve (10), inside which said sonotrode (14) is mounted.

14. Instrument according to claim 11, characterized in that said tool has the shape of scraper (16).

15. Instrument according to claim 4, characterized in that said power circuit (54) includes a power transistor (58) and a transformer (60) whose primary winding is connected to said transistor and whose secondary winding is connected to said transducer (40).

16. Instrument according to claim 15, characterized in that said mode is a traction-compression mode and its frequency fo is higher than 20 kHz.

17. Instrument according to claim 15, characterized in that said mount structure is formed of a sleeve (10), inside which said sonotrode (14) is mounted.

18. Instrument according to claim 15, characterized in that said tool has the shape of scraper (16).

19. Instrument according to claim 15, characterized in that said control circuit (12) includes means (22) for varying the passband femin–femax, and thus modifying the energy provided to the tool (16).

20. Instrument according to claim 19, characterized in that said mode is a traction-compression mode and its frequency fo is higher than 20 kHz.

* * * * *